(12) United States Patent
Yoon et al.

(10) Patent No.: US 11,534,447 B2
(45) Date of Patent: Dec. 27, 2022

(54) EMULSION COMPOSITION FOR CHEMOEMBOLIZATION AND METHOD FOR PRODUCING SAME

(71) Applicant: SAMYANG HOLDINGS CORPORATION, Seoul (KR)

(72) Inventors: Hye-Jeong Yoon, Daejeon (KR); Hye Jin Jang, Paju-si (KR)

(73) Assignee: SAMYANG HOLDINGS CORPORATION, Seoul (KR)

( * ) Notice: Subject to any disclaimer, the term of this patent is extended or adjusted under 35 U.S.C. 154(b) by 57 days.

(21) Appl. No.: 16/462,090

(22) PCT Filed: Sep. 22, 2017

(86) PCT No.: PCT/KR2017/010498
§ 371 (c)(1),
(2) Date: May 17, 2019

(87) PCT Pub. No.: WO2018/093037
PCT Pub. Date: May 24, 2018

(65) Prior Publication Data
US 2020/0268776 A1  Aug. 27, 2020

(30) Foreign Application Priority Data

Nov. 18, 2016  (KR) .................. 10-2016-0154321

(51) Int. Cl.
*A61K 31/704* (2006.01)
*A61P 35/00* (2006.01)
*A61K 9/00* (2006.01)
*A61K 9/107* (2006.01)
*A61K 9/16* (2006.01)
*A61K 31/337* (2006.01)
*A61K 31/407* (2006.01)
*A61K 31/4745* (2006.01)
*A61K 47/02* (2006.01)
*A61K 49/04* (2006.01)

(52) U.S. Cl.
CPC .......... *A61K 31/704* (2013.01); *A61K 9/0019* (2013.01); *A61K 9/107* (2013.01); *A61K 9/1635* (2013.01); *A61K 9/1647* (2013.01); *A61K 31/337* (2013.01); *A61K 31/407* (2013.01); *A61K 31/4745* (2013.01); *A61K 47/02* (2013.01); *A61K 49/0438* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 2004/0247561 A1 | 12/2004 | Seo et al. | |
| 2004/0253195 A1 | 12/2004 | Seo et al. | |
| 2005/0201972 A1* | 9/2005 | Seo .................. | C08L 53/00 424/78.27 |
| 2016/0228597 A1 | 8/2016 | Dreher | |

FOREIGN PATENT DOCUMENTS

| | | |
|---|---|---|
| CN | 1547469 A | 11/2004 |
| CN | 1964744 A | 5/2007 |
| CN | 103269690 A | 8/2013 |
| CN | 104010627 A | 8/2014 |
| CN | 105579030 A | 5/2016 |
| JP | 2005-505674 A | 2/2005 |
| KR | 10-2003-0023369 A | 3/2003 |
| KR | 10-2003-0045611 A | 6/2003 |
| KR | 10-2004-0066300 A | 7/2004 |
| KR | 10-2013-0073735 A | 7/2013 |
| KR | 10-2016-0055810 A | 5/2016 |
| WO | WO 03/022264 A1 | 3/2003 |

OTHER PUBLICATIONS

International Search Report for PCT/KR2017/010498 (PCT/ISA/210) dated Jan. 5, 2018, with English translation.
Extended European Search Report, dated Jun. 18, 2020, for European Application No, 17871977.9.
Lee et al., "Stable Paclitaxel Formulations in Oily Contrast Medium," Journal of Controlled Release, vol. 102, No. 2, 2005 (Available online Nov. 18, 2004), pp. 415-425.
Yoon et al., "Transcatheter Arterial Chemoembolization with Paclitaxel-Lipiodol Solution in Rabbit VX2 Liver Tumor," Radiology, vol. 229. No. 1, 2003 (Oct. 1, 2003), pp. 126-131.

* cited by examiner

*Primary Examiner* — Jennifer Lamberski
(74) *Attorney, Agent, or Firm* — Birch, Stewart, Kolasch & Birch, LLP

(57) ABSTRACT

The present invention relates to an emulsion composition for chemoembolization comprising a nanoparticle comprising a drug and a biocompatible polymer, a water-soluble contrast agent and a water-insoluble contrast agent, and a water-insoluble drug as well as an aqueous drug can be administered in a form of stable emulsion, and drugs are slowly released, thereby enhancing the effect of chemoembolization.

11 Claims, 3 Drawing Sheets

[FIG. 1]
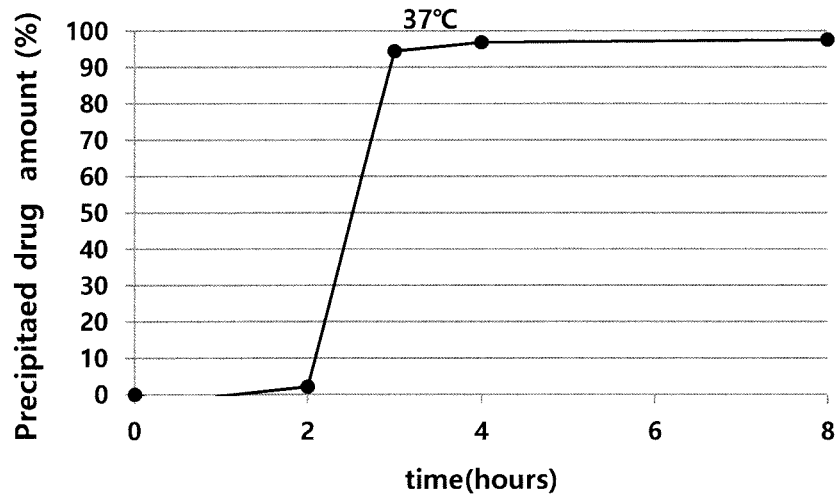
[FIG. 2]
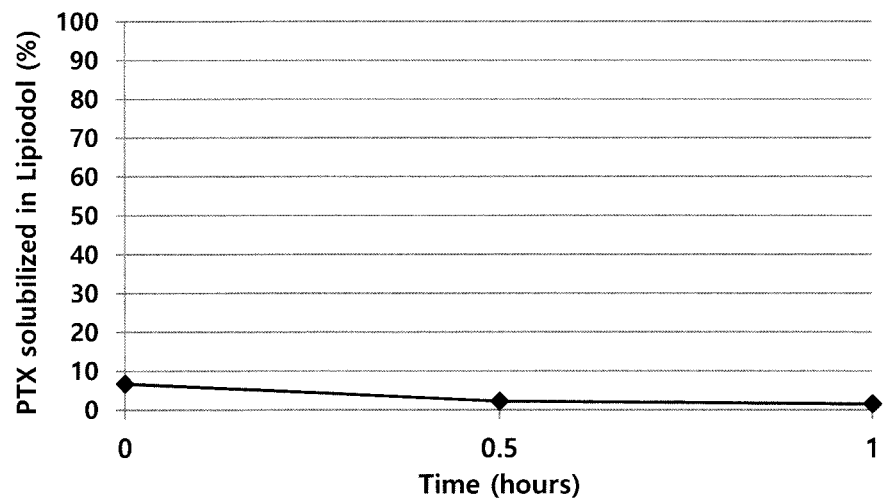

[FIG. 3]
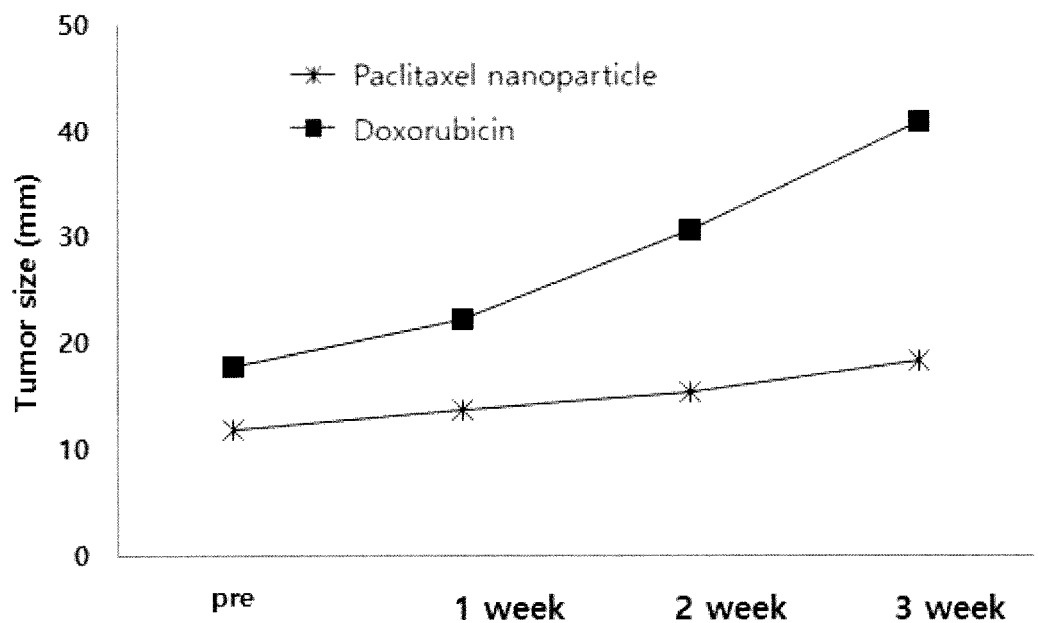
[FIG. 4]
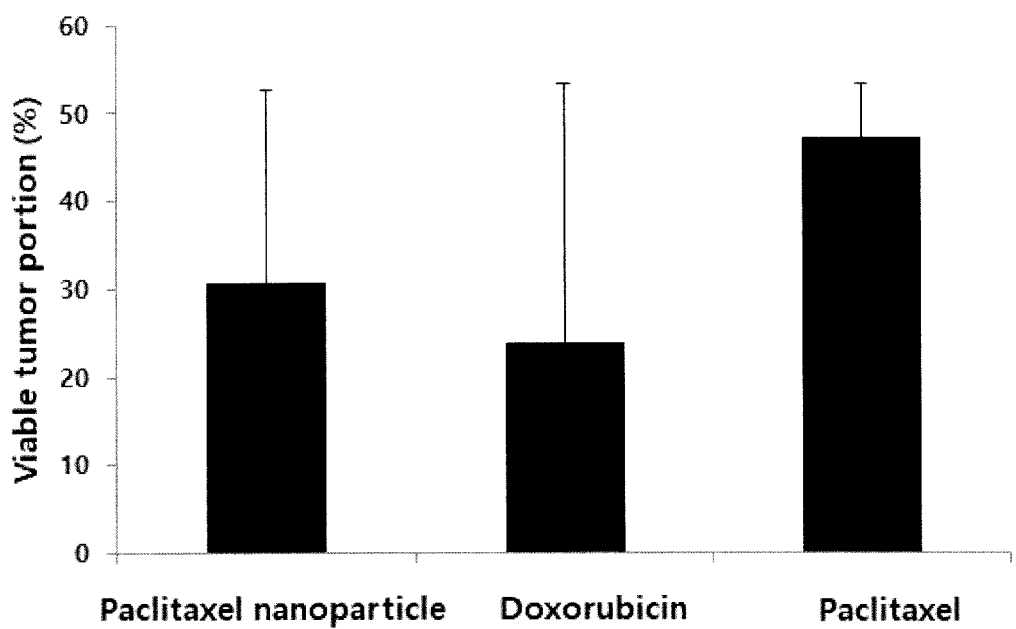

[FIG. 5]
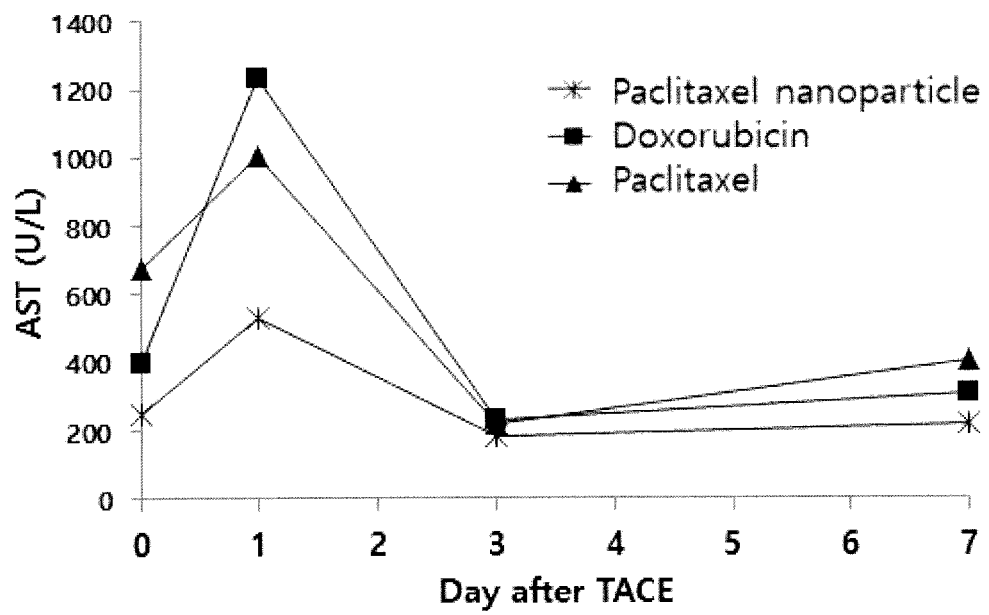
[FIG. 6]
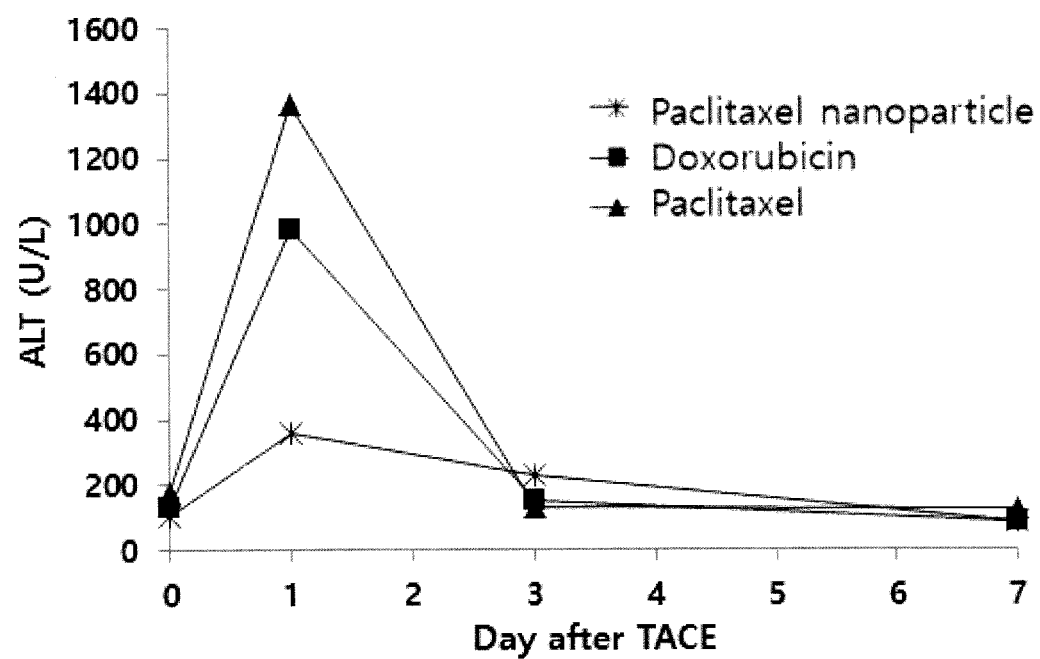

EMULSION COMPOSITION FOR CHEMOEMBOLIZATION AND METHOD FOR PRODUCING SAME

TECHNICAL FIELD

The present invention relates to an emulsion composition comprising a polymer nanoparticle comprising an anticancer agent and a biocompatible polymer, and a water-soluble contrast agent and a water-insoluble contrast agent, which is capable of being used for chemoembolization.

BACKGROUND ART

TACE (Transarterial chemoembolization) is a method for treating cancer by injecting an anticancer agent into artery leading to cancer tissue and blocking nutrition supply to the cancer tissue using embolic materials. The representative transarterial chemoembolization maximizes the topical anticancer effect against liver cancer as liver artery embolization, and in many cases, it plays a role as palliative therapy.

Liver cancer is a malignant tumor with unfavorable prognosis holding the second rank in Korea and the third rank in the world. For 70% or more of liver cancer patients, radical surgery is impossible and even if the radical surgery is performed, the probability of recurrence at other sites within 5 years is 50% or more. The possibility of responding to systemic chemotherapy in advanced liver cancer is very low within 10%, and as a non-surgical treatment as its alternative, various image-guided therapies have been developed. As the image-guided therapy applied to liver cancer, two are representative, and one is transarterial chemoembolization (TACE) which is a therapy of locally injecting an anticancer agent to liver cancer through hepatic artery and paralleling embolization to the hepatic artery, and the other is radiofrequency ablation (RFA).

Since 95% or more of blood stream supplied to liver cancer tissue is transferred to hepatic artery, but 75% or more of blood stream supplied to the surrounding healthy tissue is transferred to hepatic portal vein and only 25% is transferred to the hepatic artery, TACE is a safe and effective therapy which does not cause damage to the normal tissue.

TACE requires safe administration materials, as it is repeatedly performed commonly over 3~4 times per year. Drugs used usually for the conventional arterial chemoembolization are doxorubicin, cisplatin, epirubicin, mitoxantrone, mitomycin C, and so on. These water-soluble anticancer agents cannot be directly dissolved in a water-insoluble contrast agent, and therefore it is prepared in a form of oil-in-water or water-in-oil emulsion in which it is homogeneously distributed to a water-insoluble contrast agent (iodized oil) like Lipiodol after dissolving it in a water-soluble contrast agent like Pamiray. This emulsion is used by preparing it just before administration to a patient, since phase separation occurs in a certain time. By performing chemoembolization and additionally administering gelatin sponge particle, polyvinyl alcohol particle, and the like, ischemic necrosis of cancer tissue is facilitated and the loss of drugs is prevented. However, in the administrated emulsion, in a short time after administration, phase separation occurs and therefore the anticancer agent is absorbed at the same time, the antitumor effect is not persistent and side effects due to systemic exposure may be caused. Most of cytotoxic anticancer agents administered in TACE are metabolized in liver, and therefore the hepatotoxicity may be exhibited. Because of this, patients exhibit postembolization syndrome and the daily life is difficult and hospitalization for 2~3 days is inevitable, and thus the medical cost is high.

In recent years, a particle for chemoembolization used selectively (drug eluting bead, DEB) is a product to be administered by being prepared as non-absorbent polyvinyl alcohol and the like and adsorbing a drug to the chemoembolization particle by the ion-exchange method, and its particle size is in the range of 40~900 µm. There is an advantage in that the particle range is homogeneous compared to droplets of emulsion and there is reproducibility and the systemic expose of the drug is little as the drug is slowly released. However, as the drug is not completely released after administration, up to $28^{th}$ day after administration, only less than 50% is released, and after 90 days pass, about 90% is released, and therefore the drug is accumulated in cancer tissue at a high concentration comparatively slowly. In addition, as it takes 1~2 hours or more to absorb the drug and the particle is remained in the body after the drug is completely released, necrosis of normal tissue may be caused and TACE repeated procedure may be difficult. Moreover, as the drug cost is high compared to the conventional TACE method, the burden of expenses of patients is large.

As aforementioned, the drug used for conventional TACE and DEB is limited to water-soluble anticancer agents, and the water-insoluble anticancer agent like Paclitaxel has not been used. Paclitaxel is a cytotoxic anticancer agent of which strong antitumor effect against various cancer such as ovarian cancer, breast cancer, non-small cell lung cancer, and the like is demonstrated, but it is water-insoluble, and therefore it is impossible to administer it in a form of emulsion. In case of administering by dissolving an anticancer agent in Lipiodol, Lipiodol penetrates cancer tissue, as well as normal tissue, and it is easily accumulated in tissue other than liver, in particular, lung, and thus the toxicity may be shown. Since the viscosity is low compared to a water-in-oil emulsion comprising a water-soluble contrast agent, cancer tissue retention time is short. As a commercially available Paclitaxel injection, there is Taxol injection® developed by Bristol-Myers Squibb Company. Cremophor EL is used as a solubilizer, and it is administered in a form of microemulsion before administration. However, as the toxicity such as hypersensitive reaction due to the solubilizer, and the like is caused, it is not suitable for TACE.

DISCLOSURE

Technical Problem

An object of the present invention is to provide an emulsion composition for chemoembolization, comprising a polymer nanoparticle comprising a water-soluble anticancer agent, a water-insoluble anticancer agent or a combination thereof, and an amphiphilic block copolymer comprising a hydrophilic (A) block and a hydrophobic (B) block; a water-soluble contrast agent; and a water-insoluble contrast agent.

Other object of the present invention is to provide a preparation method of the emulsion composition for chemoembolization, and a medical composition for preventing or treating cancer comprising the emulsion composition for chemoembolization.

Technical Solution

Accordingly, to achieve the above objects, the present inventions have developed a composition which can stably administer a water-insoluble anticancer agent as well as an aqueous anticancer solution and control the release rate of drugs, by preparing an emulsion composition formed by preparing a polymer nanoparticle comprising an anticancer agent as active ingredients and an amphiphilic block copolymer, and dissolving them in a water-soluble contrast agent and then dispersing them in a water-insoluble contrast agent again.

Hereinafter, the present invention will be described in more detail.

An embodiment of the present invention provides an emulsion composition for chemoembolization, comprising a polymer nanoparticle comprising a water-soluble anticancer agent, a water-insoluble anticancer agent, or a combination thereof as active ingredients, and an amphiphilic block copolymer comprising a hydrophilic (A) block and a hydrophobic (B) block; a water-soluble contrast agent; and a water-insoluble contrast agent.

The anticancer agent used as the active ingredient includes anticancer agents which can be used for chemoembolization without limitation, and for example, the water-soluble anticancer agent may be one or more selected from the group consisting of doxorubicin, idarubicin, epirubicin, mitomycin C and irinotecan, and the water-insoluble anticancer agent may be one or more selected from the group consisting of Paclitaxel and docetaxel. Until now a water-insoluble anticancer agent, particularly, Paclitaxel has not been used for chemoembolization, but the emulsion composition of the present invention applies Paclitaxel to administer it in a form of emulsion composition for chemoembolization.

The content of the anticancer agent may be 0.01 to 30% by weight, preferably 1 to 20% by weight, more preferably 5 to 10% by weight, based on 100% by weight of the polymer nanoparticle. In addition, the anticancer agent comprised in the composition of the present invention may be comprised at a concentration of 1 to 40 mg/ml, preferably 1 to 10 mg/ml, based on the total emulsion composition.

The amphiphilic polymer comprised in the composition of the present invention is a polymer comprising a hydrophilic (A) block and a hydrophobic (B) block. The hydrophilic (A) block comprised in the amphiphilic polymer may be one or more kinds selected from the group consisting of polyalkylene glycol, polyvinyl alcohol, polyvinyl pyrrolidone, polyacrylamide and their derivatives. For example, the hydrophilic (A) block may be one or more kinds selected from the group consisting of monomethoxypolyethylene glycol, monoacetoxypolyethylene glycol, polyethylene glycol, copolymer of polyethylene and propylene glycol and polyvinyl pyrrolidone. In addition, the hydrophobic (B) block comprised in the amphiphilic polymer may be one or more kinds selected from the group consisting of polyester, polyunhydride, polyamino acid, polyorthoester and polyphosphazene, and for example, the hydrophobic (B) block may be one or more kinds selected from the group consisting of polylactide, polyglycolide, polycaprolactone, polydioxan-2-one, copolymer of polylactide and glycolide, copolymer of polylactide and polydioxan-2-one, copolymer of polylactide and polycaprolactone and copolymer of polyglycolide and polycaprolactone, or salts thereof.

The hydrophilic block (A) or hydrophobic (B) block having a number average molecular weight of 500 to 50,000 Da, preferably 1,000 to 5,000 Da may be used.

The amphiphilic block copolymer comprised in the composition of the present invention may be 1 to 30% by weight, preferably 1 to 20% by weight, based on 100% by weight of the polymer nanoparticle. In addition, the weight ratio of the hydrophilic (A) block and hydrophobic (B) block comprised in the amphiphilic block copolymer may be 2:8 to 8:2, preferably 6:4 to 4:6.

For example, as the amphiphilic block copolymer of the present invention, mPEG-poly(D,L-lactide) may be used.

The polymer nanoparticle comprised in the composition of the present invention may include a drug in the core and may be one in which the amphiphilic block copolymer forms a membrane to form a micelle. Inside of the polymer nanoparticle, when comprising a hydrophobic group of the amphiphilic block copolymer or a water-insoluble anticancer agent, the water-insoluble anticancer agent is positioned, and when comprising a hydrophilic group of the amphiphilic block copolymer or a water-soluble anticancer agent its outside, the water-soluble anticancer agent is located.

The size of the polymer nanoparticle is preferably a size which can be dissolved in a water-soluble contrast agent, and for example, the diameter of the polymer nanoparticle may be 10 to 60 nm.

The polymer nanoparticle comprised in the composition of the present invention may further comprise a polylactic acid derivative containing a carboxylic acid as an end group. When further comprising the polylactic acid derivative, the amphiphilic block copolymer and the polylactic acid derivative may be comprised at a weight ratio of 5:95 to 95:5, preferably 60:40 to 90:10.

The carboxylic acid end group of the polylactic acid may be fixed with a divalent or trivalent metal ion. The divalent or trivalent metal ion may form a harder nanoparticle by ion bonding with the carboxylic acid end group of the polylactic acid derivative. The divalent or trivalent metal ion may be combined preferably in an amount of 0.5 to 10 equivalents, preferably 0.5 to 1 equivalent, based on 1 equivalent of the carboxylic acid end group of the polylactic acid derivative.

For example, the divalent or trivalent metal ion may be one or more selected from the group consisting of calcium ($Ca^{2+}$), magnesium ($Mg^{2+}$), barium ($Ba^{2+}$), chrome ($Cr^{3+}$), iron ($Fe^{3+}$), manganese ($Mn^{2+}$), nickel ($Ni^{2+}$), copper ($Cu^{2+}$), zinc ($Zn^{2+}$) and aluminum ($Al^{3+}$), but not limited thereto.

For example, the polylactic acid derivative containing the carboxylic acid end group may be one or more selected from the group consisting of the following Formulas 1 to 6.

RO—CHZ-[A]$_n$-[B]$_m$—COOM         [Formula 1]

In the Formula 1,

A is —COO—CHZ—; and

B is —COO—CHY—, —COO—CH$_2$CH$_2$CH$_2$CH$_2$CH$_2$— or —COO—CH$_2$CH$_2$OCH$_2$; and R is a hydrogen atom, acetyl, benzoyl, decanoyl, palmitoyl, methyl or ethyl group; and Z and Y are a hydrogen atom, methyl or phenyl group, respectively; and M is Na, K, or Li; and n is an integer from 1 to 30; and m is an integer from 0 to 20.

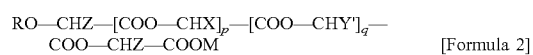

RO—CHZ—[COO—CHX]$_p$—[COO—CHY']$_q$—COO—CHZ—COOM         [Formula 2]

In the Formula 2,

X is a methyl group; and

Y' is a hydrogen atom or phenyl group; and p is an integer from 0 to 25, and q is an integer from 0 to 25, but p+q is an integer from 5 to 25; and R is a hydrogen atom, acetyl, benzoyl, decanoyl, palmitoyl, methyl or ethyl group; and M is Na, K, or Li; and Z is a hydrogen atom, methyl or phenyl group.

RO-PAD-COO—W-M'          [Formula 3]

In the Formula 3,

W-M' is

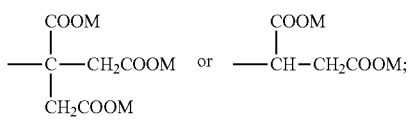

and

PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone and copolymer of D,L-lactic acid and 1,4-dioxan-2-one; and R is a hydrogen atom, acetyl, benzoyl, decanoyl, palmitoyl, methyl or ethyl group; and M is independently Na, K, or Li.

S—O-PAD-COO-Q          [Formula 4]

In the Formula 4,

S is

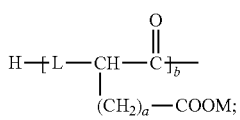

and L is -NR1- or -O-, wherein R1 is a hydrogen atom or $C_{1-10}$ alkyl; and Q is $CH_3$, $CH_2CH_3$, $CH_2CH_2CH_3$, $CH_2CH_2CH_2CH_3$, or $CH_2C_6H_5$; and a is an integer from 0 to 4; and b is an integer from 1 to 10; and M is Na, K, or Li; and PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone and copolymer of D,L-lactic acid and 1,4-dioxan-2-one.

[Formula 5]

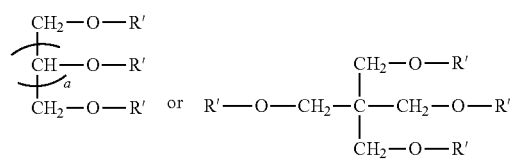

In the Formula 5,

R' is -PAD-O—C(O)—$CH_2CH_2$—C(O)—OM, wherein PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone and copolymer of D,L-lactic acid and 1,4-dioxan-2-one, and M is Na, K, or Li; and a is an integer from 1 to 4.

YO—[—C(O)—(CHX)$_a$—O—]$_m$—C(O)—R—C(O)—[—O—(CHX')$_b$—C(O)—]$_n$—OZ    [Formula 6]

In the Formula 6,

X and X' are independently a hydrogen, alkyl having 1 to 10 carbon atoms or aryl having 6 to 20 carbon atoms; and Y and Z are independently Na, K, or Li; and m and n are independently an integer from 0 to 95, and 5<m+n<100; and a and b are independently an integer from 1 to 6; and R is —(CH2)k—, divalent alkenyl having 2 to 10 carbon atoms, divalent aryl having 6 to 20 carbon atoms or combination thereof, wherein k is an integer from 0 to 10.

The water-soluble contrast agent used in the emulsion composition of the present invention is an aqueous solution comprising iodide, and preferably iopamidol and the product name, Pamiray™ may be used. In addition, the water-insoluble contrast agent is iodized oil, and it may be one or more selected from the group consisting of poppy fruit-derived iodized oil, soybean-derived iodized oil and ethiodol, and preferably, as the poppy fruit-derived iodized oil, the product name Lipiodol™ may be used.

The viscosity of the water-insoluble contrast agent and water-soluble contrast agent used in the present invention is 10 to 40 mPa at 37° C., respectively. This is for easy blood vessel pass and securement of enough time for the emulsion to stay in cancer tissue, when administering the emulsified anticancer agent nanoparticle. More preferably, the viscosity of the water-insoluble contrast agent and water-soluble contrast agent is 20 to 30 mPa at 37° C., respectively.

Preferably, the volume ratio of the water-soluble contrast agent in which the polymer nanoparticle is dissolved and water-insoluble contrast agent may be 1:2 to 1:10, and more preferably it may be 1:3 to 1:5.

The emulsion composition according to the present invention may be a form of water-in-oil emulsion by that the solution in which the nanoparticle is dissolved in the water-soluble contrast agent forms droplets in the water-insoluble contrast agent. Accordingly, when administering the emulsion composition in the body, the drug release may be primarily controlled by droplets of the emulsion and the drug release may be secondarily controlled by the nanoparticle. Therefore, the systemic toxicity caused by rapid drug release can be reduced, and in particular, the drug release is sustained in cancer tissue, thereby enhancing the antitumor effect.

Preferably, the size of droplets of the emulsion composition may be 10 to 100 μm, preferably 20 to 40 μm.

The viscosity of the emulsion composition may be used as adjusted to be suitable for chemoembolization, and it may be 20 to 50 mPa, preferably 25 to 45 mPa at 37° C.

The chemoembolization as the use of the emulsion composition may be preferably transarterial chemoembolization (TACE), which is a method for treating cancer by injecting an anticancer agent to artery leading to cancer tissue and blocking nutrition supply to cancer tissue using embolic materials.

As another embodiment, the present invention relates to a medical composition for preventing or treating cancer, comprising the emulsion composition. The cancer includes angiogenesis dependent one, and preferably, it may be one or more selected from the group consisting of liver cancer, ovarian cancer, breast cancer and non-small cell lung cancer, and more preferably it is liver cancer. The inside diameter of hepatic portal vein is 50 to 100 μm, and the inside diameter of hepatic portal vein end is 15 to 50 μm, and the hepatic sinusoid is 5 to 8 μm, and the terminal postcapillary venule is 25 μm or less, and the hepatic artery is 35 to 45 μm. The composition of the present invention may have the selectivity to the vessel having the same inside diameter as the hepatic artery due to the size characteristics of droplets particularly, and it is difficult to enter the very narrow vessel like hepatic sinusoid.

The medical composition of the present invention is characterized by being administered within 0 to 2 hours, preferably 0 to 1 hour after emulsion preparation, and it has excellent stability as the movement of the anticancer agent in the polymer nanoparticle is maintained low for a long time compared to the conventional composition for chemoembolization.

The dosage of the medical composition may be controlled by a doctor's decision depending on patients' age, gender, weight and severity of symptoms, and for example, repeated treatment is possible per at least 3 months. It may be administered for example, in an amount of 5 to 15 ml once, through the artery supplying blood to solid cancer like hepatic artery.

As an embodiment, the present invention comprises a method for performing chemoembolization using the emulsion composition to an animal, preferably, an animal except for human. The matters relating to the emulsion composition may be applied to the method of using the emulsion composition.

As other embodiment, the present invention provides a preparation method of an emulsion composition for chemoembolization, comprising a step of preparing a nanoparticle comprising a water-soluble anticancer agent, a water-soluble anticancer agent or a combination thereof as an active ingredient, and an amphiphilic block copolymer comprising a hydrophilic (A) block and a hydrophobic (B) block; a step of dissolving the polymer nanoparticle to a water-soluble contrast agent; and a step of preparing emulsion by dispersing the polymer nanoparticle solution dissolved in the water-soluble contrast agent to a water-insoluble contrast agent.

The matters relating to the emulsion composition may be applied for the preparation method of emulsion composition.

In the step of preparing a nanoparticle, a nanoparticle may be prepared by dissolving a drug and a biocompatible polymer in an organic solvent and then drying it. The emulsion composition may be prepared by dissolving the prepared nanoparticle to a water-soluble contrast agent and dispersing it to a water-insoluble contrast agent so that the solution in which the nanoparticle is dissolved in the water-soluble contrast agent forms droplets.

The organic solvent may be one or more selected from the group consisting of methanol, ethanol, methylene chloride and acetonitrile, but not limited thereto.

The step of preparing a nanoparticle specifically, an organic solvent, in which an anticancer agent and an amphiphilic block copolymer are dissolved, is decompressed and heated to remove a solvent, thereby obtaining a homogeneous matrix, and then it is dissolved again by adding purified water for injection. After that, in case of using polylactic acid sodium salt or polymandelic acid sodium salt, it may be prepared by adding the divalent metal to form an ion bond and obtain a hard particle and then sterilizing by filtration and lyophilizing.

As specific one embodiment according to the present invention, the solution prepared by the method may be stable at 25° C. for 5 hours or more and may be stable at 37° C. for 2 hours or more, and the concentration of the drug in the solution may be 1 to 40 mg/ml, more preferably 10 to 30 mg/ml.

In the step of preparing emulsion, as the method for dispersing the solution in a water-insoluble contrast agent, a pump method using a 3-way stopcock, a method using ultrasonic waves, and so on may be used, but not limited thereto.

An embodiment of the present invention provides a method for preventing or treating cancer comprising a step of administering an emulsion composition for chemoembolization, comprising a polymer nanoparticle a water-soluble anticancer agent, a water-insoluble anticancer agent or a combination thereof as active ingredients, and an amphiphilic block copolymer comprising a hydrophilic (A) block and a hydrophobic (B) block; a water-soluble contrast agent; and a water-insoluble contrast agent, to a subject in need thereof.

Herein, "subject" includes any human or non-human animal. The term "non-human animal" includes non-human vertebrates, for example, non-human primates, sheep, dog and rodents, for example, mouse, rat and guinea pig, but not limited thereto.

Herein "anticancer agent" enhances cancer regression in a subject. In other embodiment, an effective amount for treatment of drug enhances cancer regression to the point where cancer is removed. "Enhance cancer regression" means that when administering an effective dose of anticancer agent alone or administering it in combination with other anticancer agent, the tumor growth or size is reduced, or the tumor is necrosed, or the severity of at least one of disease symptoms is reduced, or the frequency and sustainability of the period without disease symptoms are increased, or damage or disorders due to pain of diseases are prevented.

The method of the present invention may be applied for angiogenesis dependent cancer, preferably, one or more selected from the group consisting of liver cancer, ovarian cancer, breast cancer and non-small cell lung cancer, and more preferably it may be applied for liver cancer. The emulsion composition may be administered intra-arterially, and for example, the cancer is liver cancer, and the intra-arterial administration may be hepatic artery infusion or transarterial chemoembolization.

Advantageous Effects

According to the emulsion composition of the present invention, an anticancer agent can be administered in a form of water-in-oil emulsion, and therefore a water-insoluble anticancer agent as well as a water-soluble anticancer agent can be used for chemoembolization, and it can have selectivity to bigger artery blood vessels than narrow artery blood vessels.

The emulsion composition according to the present invention is prepared as an amphiphilic block copolymer, and therefore it has excellent biocompatibility and drugs are slowly released throughout twice, and thus the antitumor effect is sustained and the systemic toxicity is low.

BRIEF DESCRIPTION OF DRAWINGS

FIG. 1 shows the change in precipitation amount of a drug after storing a Paclitaxel polymer nanoparticle solution.

FIG. 2 shows the drug release test result of the Paclitaxel polymer nanoparticle emulsion.

FIG. 3 shows the change in size of cancer tissues after administering the Paclitaxel polymer nanoparticle emulsion and doxorubicin emulsion.

FIG. 4 shows the viable tumor portion result after administering the Paclitaxel polymer nanoparticle emulsion, doxorubicin emulsion and Paclitaxel solution.

FIG. 5 shows the AST change after TACE with the Paclitaxel polymer nanoparticle emulsion, doxorubicin emulsion and Paclitaxel solution.

FIG. 6 shows the ALT change after TACE with the Paclitaxel polymer nanoparticle emulsion, doxorubicin emulsion and Paclitaxel solution.

MODE FOR INVENTION

Hereinafter, the present invention will be described in detail by examples. However, the following examples are intended to illustrate the present invention only, and the present invention is not limited by the following examples.

<Example 1> Polymer Nanoparticle Preparation

Paclitaxel 450 mg, mPEG-poly(D,L-lactide) 7600 mg and polylactic acid sodium salt 1642 mg were weighed and put into a round flask and completely dissolved in a small amount of dichloromethane, and then the solvent was completely removed at the temperature of 40° C. using a rotary evaporator. Purified water was added thereto and it was completely dissolved and sterile filtrated and the drug concentration was to be 20 mg/ml, and then it was lyophilized, thereby preparing a polymer nanoparticle.

<Example 2> Preparation of Solution of Nanoparticle and Water-Soluble Contrast Agent and Confirmation of Solubility To Pamiray 250™ (Dongkook pharmaceutical) as a water-soluble contrast agent, the Paclitaxel polymer nanoparticle prepared in Example 1 was dissolved to make the Paclitaxel concentration 20 mg/ml. The prepared solution was stirred at 200 RPM at the temperature of 37° C. and the precipitation amount of the drug over time was quantified, thereby confirming the change in solubility of the drug. The test solution was aliquoted 500μℓ each, and 0, 0.5, 1, 2, 3, 4 and 8 hours later, the test solution was filtrated (Millex HV, PVDF, 0.22 μm) and the drug concentration comprised in the nanoparticle in the filtrated solution was measured by HPLC. The HPLC measurement conditions were shown in the following Table 1.

TABLE 1

| Column | poroshell 120 PFP, 4.6 mm × 150 mm, 2.7 μm |
|---|---|
| Flow rate | 0.6 ml/min |
| Moving bed | Acetonitrile/water (45/55, V/V) |
| Detector and wavelength | UV, 227 nm |
| Column temperature | 30° C. |

The change in the drug precipitation amount after storing the Paclitaxel nanoparticle solution at 37° C. was shown in FIG. 1, and it was confirmed that the solubility of the drug at the temperature of 37° C. by 2 hours after preparation was maintained to about 20 mg/ml.

<Example 3> Water-in-Oil (W/O) Emulsion Preparation and Stability Evaluation

The solution of Example 2 and Lipiodol™ as the water-insoluble contrast agent were filled into a syringe respectively so that the volume ratio was 1:4, and then pumping was carried out using a 3-way stopcock 50 times or more, to prepare emulsion.

In order to evaluate the stability of the prepared emulsion, the size change of droplets was observed by observing with an optical microscope at 25° C. over time. As a result, it could be confirmed that uniform droplets were formed in a size of 10 to 30 μm right after preparation.

In addition, in order to confirm the amount of Paclitaxel which was moved to the water-insoluble contrast agent, Lipiodol layer, as the continuous phase in the prepared emulsion, by aliquoting 500 μℓ each and storing at the temperature of 37° C. for 1 hour while stirring, and then ultrafiltrating (molecular weight cut off: 100 kDa), the amount of the drug in the Lipiodol layer was HPLC analyzed under the analysis conditions of Table 1.

The result was shown in FIG. 2, and it was confirmed that the Paclitaxel moved to the Lipiodol layer right after preparation and 1 hour later was less than 10% of the total.

<Example 4> Chemoembolization in Liver Cancer Animals 4.1 Animal Model Manufacturing After exposing left lobe of liver by performing laparotomy to Sprague Dawley rat, $1 \times 10^7$ of N1-S1 rat hepatoma tumor cells (Seoul National University Hospital) were inoculated to manufacture a liver cancer animal model. 12 days later, MRI was carried out to confirm tumor formation and the size of tumor was measured.

4.2 Chemoembolization

After the carotid artery of rat prepared in Example 4.1 was exfoliated and tied up with thread, thereby preventing hemostasis, the carotid artery was punctured using 24G medicut. Then, microguidewire and microcatheter were sequentially inserted. After implementing abdominal aorta angiography under induction of fluoroscopy, the emulsion of Example 3 was administered into liver artery, and doxorubicin as a control drug was dissolved in Pamiray 250™ as a water-soluble contrast agent at a concentration of 20 mg/ml, and the solution in which this and Lipiodol were mixed at a volume ratio of 1:4 (Pamiray:Lipiodol), and one in which Paclitaxel was dissolved in Lipiodol™ as a water-insoluble contrast agent were administered at the same dose. Then, in the computed tomography and magnetic resonance imaging, it was confirmed that Lipiodol was deposited inside the tumor, and after inserting a catheter through the carotid artery of the model mouse, chemoembolization was conducted.

4.3 Cancer Tissue Size Measurement one week, 2 weeks and 3 weeks later after conducting chemoembolization of Example 4.2, the size change of cancer tissue was measured using magnetic resonance, and the result was shown in FIG. 3. As shown in FIG. 3, it was confirmed that when administering the Paclitaxel polymer nanoparticle as emulsion using a water-soluble contrast agent and an oil contrast agent, the size of cancer tissue was not increased than doxorubicin emulsion.

4.4 Viable Tumor Portion Measurement

On the 7th day after conducting TACE with the Paclitaxel polymer nanoparticle emulsion prepared in Example 2 and the doxorubicin emulsion and Paclitaxel solution as comparative examples, the normal liver tissue and cancer tissue were isolated by conducting biopsy. The isolated tissue was stained with hematoxylin and eosin and thereby the viable tumor portion was confirmed and the result was shown in FIG. 4.

As shown in FIG. 4, it was confirmed that the viable tumor portion of the Paclitaxel polymer nanoparticle emulsion administration group was similar to the water-soluble anticancer agent, doxorubicin emulsion control group, despite of using a water-insoluble anticancer agent, and the tumor survival portion was low when comparing with the Paclitaxel solution-administered control group.

4.5 AST and ALT Measurement

In order to confirm the hepatotoxicity, AST and ALT were measured by collecting blood before and 1, 3 and 7 days after TACE to the Paclitaxel polymer nanoparticle emulsion, doxorubicin emulsion and Paclitaxel solution.

The measurement result was shown in FIG. 5 and FIG. 6, and it was confirmed that AST and ALT were significantly increased on the 1st day of TACE in all test groups, but they were almost completely recovered on the 3rd day. In particular, it was confirmed that the increase of AST and ALT on the 1st day of administration was relatively small, when administering the Paclitaxel nanoparticle emulsion formulation, compared to administering the Paclitaxel Lipiodol solution.

The invention claimed is:

1. An emulsion composition for chemoembolization, comprising
    a polymer nanoparticle comprising a water-soluble anticancer agent, a water-insoluble anticancer agent, or a combination thereof as active ingredients, and an amphiphilic block copolymer comprising a hydrophilic (A) block and a hydrophobic (B) block;
    a water-soluble contrast agent; and
    a water-insoluble contrast agent,
    wherein the hydrophilic (A) block is one or more selected from the group consisting of monomethoxypolyethylene glycol, monoacetoxypolyethylene glycol, polyethylene glycol, copolymer of polyethylene and propylene glycol, and polyvinyl pyrrolidone, and
    the hydrophobic (B) block is one or more selected from the group consisting of polylactide, polyglycolide, polycaprolactone, polydioxan-2-one, copolymer of polylactide and glycolide, copolymer of polylactide and polydioxan-2-one, copolymer of polylactide and polycaprolactone and copolymer of polyglycolide and polycaprolactone; and
    the water-soluble contrast agent is iopamidol, and the water-insoluble contrast agent is one or more selected from the group consisting of poppy fruit-derived iodized oil, soybean-derived iodized oil and ethiodol, wherein the diameter of the polymer nanoparticle is 10 nm to 60 nm.

2. The emulsion composition for chemoembolization according to claim 1, wherein the number average molecular weight of hydrophilic (A) block or hydrophobic (B) block is 500 to 50,000 Da.

3. The emulsion composition for chemoembolization according to claim 1, wherein the weight ratio of the hydrophilic (A) block and hydrophobic (B) block is 2:8 to 8:2.

4. The emulsion composition for chemoembolization according to claim 1, wherein the polymer nanoparticle further comprises a polylactic acid derivative containing a terminal group of a carboxylic acid.

5. The emulsion composition for chemoembolization according to claim 4, wherein the polylactic acid derivative containing a terminal group of carboxylic acid is one or more selected from the group consisting of the compounds of Formulas 1 to 6:

RO—CHZ-[A]$_n$-[B]$_m$—COOM            [Formula 1]

in the Formula 1,
A is —COO—CHZ—; and
B is —COO—CHY—, —COO—CH$_2$CH$_2$CH$_2$CH$_2$CH$_2$— or —COO—CH$_2$CH$_2$OCH$_2$; and
R is a hydrogen atom, acetyl, benzoyl, decanoyl, palmitoyl, methyl or ethyl group; and
Z and Y are independently a hydrogen atom, methyl or phenyl group; and
M is Na, K, or Li; and n is an integer from 1 to 30; and m is an integer from 0 to 20;

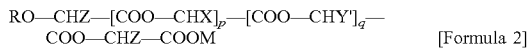
RO—CHZ—[COO—CHX]$_p$—[COO—CHY']$_q$—COO—CHZ—COOM            [Formula 2]

in the Formula 2,
X is a methyl group; and
Y' is a hydrogen atom or phenyl group; and
p is an integer from 0 to 25, and q is an integer from 0 to 25, on the proviso that sum of p and q is an integer from 5 to 25; and
R is a hydrogen atom, acetyl, benzoyl, decanoyl, palmitoyl, methyl or ethyl group; and
M is Na, K, or Li; and
Z is a hydrogen atom, methyl or phenyl group;

RO-PAD-COO—W-M'            [Formula 3]

in the Formula 3,
W-M' is

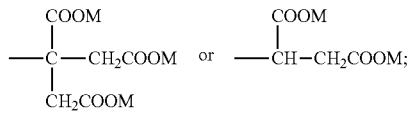

and
PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone and copolymer of D,L-lactic acid and 1,4-dioxan-2-one; and
R is a hydrogen atom, acetyl, benzoyl, decanoyl, palmitoyl, methyl or ethyl group; and
M is independently Na, K, or Li;

S—O-PAD-COO-Q            [Formula 4]

in the Formula 4,
S is

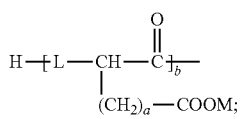

and L is -NR1- or -O-, wherein R1 is a hydrogen atom or $C_{1-10}$ alkyl; and Q is $CH_3$, $CH_2CH_3$, $CH_2CH_2CH_3$, $CH_2CH_2CH_2CH_3$, or $CH_2C_6H_5$; and a is an integer from 0 to 4; and b is an integer from 1 to 10; and M is Na, K, or Li; and PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone and copolymer of D,L-lactic acid and 1,4-dioxan-2-one.

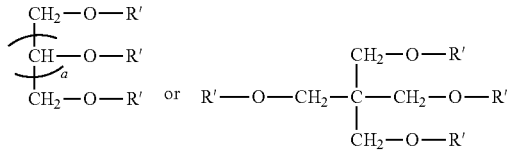 [Formula 5]

in the Formula 5, R' is -PAD-O—C(O)—CH$_2$CH$_2$—C(O)—OM, wherein PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone and copolymer of D,L-lactic acid and 1,4-dioxan-2-one, and M is Na, K, or Li; and a is an integer from 1 to 4.

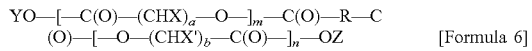 [Formula 6]

in the Formula 6,

X and X' are independently a hydrogen, alkyl having 1 to 10 carbon atoms or aryl having 6 to 20 carbon atoms; and Y and Z are independently Na, K, or Li; and m and n are independently an integer from 0 to 95 to meet 5<m+n<100; and a and b are independently an integer from 1 to 6; and R is —(CH2)k—, divalent alkenyl having 2 to 10 carbon atoms, divalent aryl having 6 to 20 carbon atoms or combination thereof, wherein k is an integer from 0 to 10.

6. The emulsion composition for chemoembolization according to claim 4, wherein the terminal group of carboxylic acid in the polylactic acid derivative is fixed with a divalent or trivalent metal ion.

7. The emulsion composition for chemoembolization according to claim 6, wherein the divalent or trivalent metal ion is selected from the group consisting of calcium ($Ca^{2+}$), magnesium ($Mg^{2+}$), barium ($Ba^{2+}$), chrome ($Cr^{3+}$), iron ($Fe^{3+}$), manganese ($Mn^{2+}$), nickel ($Ni^{2+}$), copper ($Cu^{2+}$), zinc ($Zn^{2+}$) and aluminum ($Al^{3+}$).

8. The emulsion composition for chemoembolization according to claim 1, wherein the viscosity of the water-soluble contrast agent or water-insoluble contrast agent is 10 to 40 mPa at 37° C.

9. The emulsion composition for chemoembolization according to claim 1, wherein the polymer nanoparticle is dissolved in the water-soluble contrast agent so that the concentration of anticancer agent is 1 to 40 mg/ml based on the total emulsion composition.

10. The emulsion composition for chemoembolization according to claim 9, wherein the volume ratio of the water-soluble contrast agent in which the polymer nanoparticle is dissolved and water-insoluble contrast agent is 1:2 to 1:10.

11. The emulsion composition for chemoembolization according to claim 1, wherein the viscosity of the emulsion composition is 20 to 50 mPa at 37° C.

* * * * *